United States Patent [19]

Mues et al.

[11] 4,256,740
[45] Mar. 17, 1981

[54] SYNERGISTIC ARTHROPODICIDAL COMPOSITIONS CONTAINING α-SUBSTITUTED-3,4-METHYLENEDIOXY-PHENYLACETONITRILES

[75] Inventors: Volker Mues, Wuppertal; Wolfgang Behrenz, Overath; Klaus Ditgens; Thomas Schmidt, both of Wuppertal, all of Fed. Rep. of Germany

[73] Assignee: Bayer Aktiengesellschaft, Leverkusen, Fed. Rep. of Germany

[21] Appl. No.: 37,544

[22] Filed: May 9, 1979

Related U.S. Application Data

[62] Division of Ser. No. 851,571, Nov. 14, 1977, Pat. No. 4,182,771.

[30] Foreign Application Priority Data

Dec. 1, 1976 [DE] Fed. Rep. of Germany ....... 2654348
Jan. 15, 1977 [DE] Fed. Rep. of Germany ....... 2701586

[51] Int. Cl.³ ............... A01N 37/10; A01N 43/30; A01N 57/16; A01N 57/28
[52] U.S. Cl. ................... 424/200; 424/188; 424/202; 424/203; 424/210; 424/212; 424/216; 424/219; 424/220; 424/225; 424/274; 424/305; 424/306; 424/308; 424/211; 424/214; 424/217; 424/218; 424/222; 424/282

[58] Field of Search ............... 424/274, 282, 200, 219, 424/188, 305, 306, 308, 285, 203, 210, 212, 216, 220

[56] References Cited

U.S. PATENT DOCUMENTS

| 3,268,398 | 8/1966 | Kato et al. ..................... 424/274 |
| 3,338,783 | 8/1967 | Popjak ........................... 424/282 |

*Primary Examiner*—Allen J. Robinson

[57] ABSTRACT

Synergistic arthropodicidal compositions comprising a carbamate, carboxylic acid ester or phosphate ester and an α-substituted-3,4-methylenedioxyphenylacetonitrile of the formula

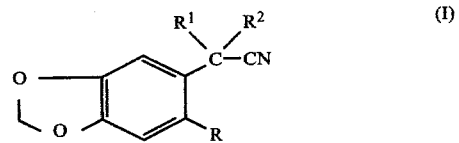

in which
R represents hydrogen, alkyl, alkenyl, halogen or nitro,
$R^1$ represents alkyl or hydrogen, and
$R^2$ represents aralkyl, alkyl, alkenyl or cycloalkyl or may represent hydrogen, provided that R represents alkyl, alkenyl or nitro, or
$R^1$ and $R^2$ together represent an alkylene radical.

18 Claims, No Drawings

SYNERGISTIC ARTHROPODICIDAL COMPOSITIONS CONTAINING α-SUBSTITUTED-3,4-METHYLENEDIOXY-PHENYLACETONITRILES

This is a division of application Ser. No. 851,571, filed Nov. 14, 1977, now U.S. Pat. No. 4,182,771 issued Jan. 8, 1980.

The present invention relates to new arthropodicidal, especially insecticidal and acaricidal, synergistic combinations of certain benzodioxoles (some of which are known), and certain other, known, pesticidal active compounds.

It has already been disclosed that benzodioxole derivatives, for example α,α-dimethyl-(3,4-methylenedioxyphenyl)-acetonitrile and α,α-ethylene-(3,4-methylenedioxyphenyl)-acetonitrile, may be used as intermediates for the preparation of pharmaceuticals (see German Offenlegungsschrift (German Published Specification) No. 2,215,496 and J. of Org. Chem. 1972, pages 977–982).

The following insecticidal active compounds or groups of active compounds have also been disclosed:

(A) carbamates, such as, for example, 2-isopropoxy-phenyl N-methyl-carbamate, 3,4,5-trimethyl-phenyl N-methyl-carbamate, 1-naphthyl N-methyl-carbamate, 2,3-dihydro-2,2-dimethyl-7-benzofuranyl N-methyl-carbamate, 2-[1,3-dioxolan-2-yl-phenyl] N-methyl-carbamate and 2,2-dimethyl-1,3-benzodioxol-4-yl N-methyl-carbamate, (B) carboxylic acid esters, such as, for example, 2,3,4,5-tetrahydrophthalimido-methyl chrysanthemate and (5-benzyl-3-furyl)-methyl-2,2-dimethyl-3-(2-methylpropenyl)-cyclopropane-carboxylate, and (C) phosphoric acid esters, such as, for example, O,O-dimethyl-O-(2,2-dichlorovinyl)-phosphoric acid esters.

Furthermore, synergistic mixtures of carbamates, for example 2-isopropoxy-phenyl-N-methylcarbamate, or of phosphoric acid esters, for example O,O-diethyl-O-(2-isopropyl-4-methylpyridine-dimethyl-[6]-phosphorothioate, or of natural or synthetic pyrethroids with piperonyl ethers, such as, for example, α-[2-(2-butoxy-ethoxy)-ethoxy]-4,5-methylenedioxy-2-propyl-toluene, are known (see Bull. Org. Health Org. 1966, 35, pages 691–708, Schrader, G.: Die Entwicklung neuer insektizider Phosphorsäureester (The Development of new Insecticidal Phosphoric Acid Esters), 1963, page 158; Perkov, W.: Die Insektizide (The Insecticides), 1966, pages 516–524). However, the activity of these synergistic active-compound combinations is not satisfactory. Hitherto, only α-[2-(2-butoxy-ethoxy)-ethoxy]-4,5-methylenedioxy-2-propyl-toluene has essentially achieved a certain practical importance.

The present invention now provides an arthropodicidal composition containing as active ingredients (i) a benzodioxole derivative of the general formula

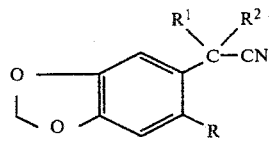

(I)

in which
R represents hydrogen, alkyl, alkenyl, halogen or nitro, $R^1$ represents alkyl or hydrogen, and
$R^2$ represents aralkyl, alkyl, alkenyl or cycloalkyl or may represent hydrogen, provided that R represents alkyl, alkenyl or nitro, or
$R^1$ and $R^2$ together represent an alkylene radical, and (ii) at least one compound selected from (A) carbamates, (B) carboxylic acid esters (including the natural and synthetic pyrethroids) and (C) phosphoric acid esters, alone or in admixture with a solid or liquid or liquefied gaseous diluent or carrier.

Surprisingly, the insecticidal and/or acaricidal action of the active-compound combinations according to the invention is substantially higher than the action of the individual components or the sum of the actions of the individual components. Furthermore, it is substantially higher than the action of the active-compound combination, which is already known, of 2-isopropoxy-phenyl N-methylcarbamate and piperonyl butoxide. In addition, the benzodioxole derivatives exhibit excellent synergistic activity not only with one class of active compounds but with active compounds from the most diverse chemical groups of substances. Thus the synergistic mixtures, according to the invention, containing benzodioxole derivatives represent a valuable enrichment of the art.

The formula (I) provides a general definition of the benzodioxole derivatives to be used in the compositions according to the invention. Preferably, however, in the formula (I),
R represents hydrogen, chlorine, bromine, nitro or straight-chain or branched alkyl with 1 to 6 (especially 1 to 4) carbon atoms, or straight-chain or branched alkenyl with 2 to 6 carbon atoms (especially propenyl, allyl or isopropenyl),
$R^1$ represents hydrogen or straight-chain or branched alkyl with 1 to 3 carbon atoms (especially methyl),
$R^2$ represents straight-chain or branched alkyl or alkenyl with up to 6 (especially with up to 4) carbon atoms, cycloalkyl with 3 to 8 (especially 4 to 6) carbon atoms or benzyl or may represent hydrogen, provided that R represents nitro, alkyl or alkenyl, or $R^1$ and $R^2$ together represent an alkylene radical with 2 to 8 (especially 2 to 5) carbon atoms.

Examples which may be mentioned of the benzodioxole derivatives of the formula (I) are: α-methyl-, α-ethyl-, α-n-propyl-, α-iso-propyl-, α-n-butyl-, α-iso-butyl-, α-sec.-butyl-, α-tert.-butyl-, α-allyl-, α-benzyl-, α,α-dimethyl-, α-methyl-α-ethyl-, α-methyl-α-n-propyl-, α-methyl-α-iso-propyl-, α,α-ethylene-, α,α-trimethylene-, α, α-tetramethylene, α-cyclopropyl- and α-cyclohexyl-(3,4-methylenedioxyphenyl)-acetonitrile; the derivatives substituted, in each case, in the 6-position by chlorine, bromine, methyl, ethyl, n-propyl, isopropyl, tert.-butyl, allyl, propenyl, iso-propenyl or nitro; and 6-nitro-, 6-methyl-, 6-ethyl-, 6-n-propyl-, 6-isopropyl-, 6-tert.-butyl-, 6-allyl-, 6-propenyl- or 6-isopropenyl-(3,4-methylenedioxyphenyl)-acetonitrile.

Some of these compounds are new, but they can be prepared in accordance with processes which are known from the literature [see, for example, German Offenlegungsschrift (German Published Specification) No. 2,215,496 and No. 2,335,347, British Patent Specification 1,109,527, J. Amer. Chem. Soc., 64 (1942), pages 2,486–2,487 and J. Org. Chem., 1972, pages 977–982].

The new compounds can be prepared, in the case where R is hydrogen, halogen or nitro, by reducing 3,4-methylenedioxy-benzaldehyde to piperonyl alcohol, converting this into the corresponding halide and reacting the halide with a cyanide to give 3,4-methylenedioxyphenylacetonitrile [see von Braun and Wirz, Ber. dt. Chem. Ges. 60, 110 (1927)]. This compound can then be alkylated to give the compounds of the formula (V) indicated below, in accordance with the customary processes which are known from the literature [see Dehmlow, New Synthetic Methods, Vol. 1, 19 (1975); Makosza et al., Chimie et Industrie (Paris) 93, 537 (1965); Makosza, Pure Appl. Chem., 43,439 (1975) and Makosza and Jonczyk, Org. Syn., 55, 91 (1976)]. The compounds of the formula (V) can then be halogenated, for example with sulphuryl chloride or bromine or nitrated, for example with a mixture of concentrated sulphuric acid and nitric acid.

The following equation illustrates the course of the reaction:

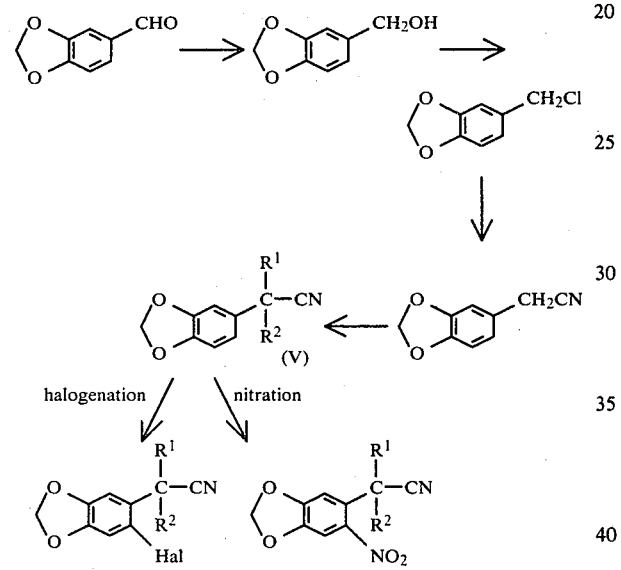

It is also possible to halogenate 3,4-methylenedioxybenzaldehyde [see Dallacker, Liebigs Ann. Chem. 633, 14 (1960) and Weisse, Ber. dt. Chem. Ges. 43, 2605 (1910)] and then to proceed in the manner described. This method of sequence, however leads to poor yields.

The synthesis proceeds via the following stages when R stands for (a) n-propyl:

safrol→dihydrosafrol→6-chloromethyldihydrosafrol→6-cyanomethyldihydrosafrol→desired compound, (b) allyl: safrol→6-chloromethylsafrol→6-cyanomethylsafrol→desired α-alkylacetonitriles, (c) propenyl: isosafrol→6-chloromethylisosafrol→6-cyanomethylsafrol→desired compound (the subsequent isomerization of the alkyl compound indicated under (b) is more advantageous) and (d) tert.-butyl: 4-tert.-butylpyrocatechol→3,4-methylenedioxy-tert.-butylbenzene→6-chloromethyl-3,4-methylenedioxy-tert.-butylbenzene→6-cyanomethyl-3,4-methylenedioxytert.-butylbenzene→desired compound.

The toluenes and ethylbenzenes according to the invention can be prepared analogously from 4-methyl- or 4-ethyl-pyrocatechol respectively (compare with the 6-chloromethyl compounds in U.S. Pat. No. 2,485,600 and No. 2,485,680).

The individual stages of the synthesis paths given are known or are carried out in accordance with procedures which are in themselves known. For example, the 6-chloromethyl compounds serving, in each case, as intermediates can be prepared in accordance with the processes indicated in U.S. Pat. No. 2,485,600 and No. 2,485,680.

Preferred carbamates (A) are those of the general formula

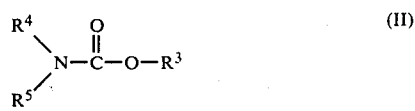

in which $R^3$ represents aryl, a heterocyclic radical or an oxime radical, $R^4$ represents hydrogen or alkyl with 1–4 C atoms and $R^5$ represents alkyl or alkylcarbonyl with 1 to 6 C atoms in the alkyl radical [which can be optionally substituted by hydroxyl or methylthio] or the radical —S—Y, wherein Y represents an aliphatic radical with 1–4 C atoms [which is optionally substituted by halogen (especially $CCl_3$ and $CF_3$)], or an aryl radical (especially phenyl) [which is optionally (indeed preferably) substituted by CN, halogen (especially chlorine), methyl, trihalogenomethyl, trifluoromethylmercapto or $NO_2$], or methoxycarbonyl or the radical

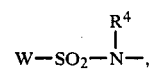

wherein

W represents alkyl, halogenoalkyl, alkylamino or dialkylamino or an aryl radical [which is optionally (indeed preferably) substituted by halogen, trihalogenomethyl, CN, methyl or nitro].

Particularly preferred carbamates (II) are those in which $R^3$ represents phenyl or naphthyl [either of which is optionally substituted by alkyl, alkenyl, alkoxy or alkylmercapto with up to 5 C atoms in each case, dialkylamino or dialkylamino with up to 3 C atoms per alkyl or alkenyl part, halogen (especially chlorine), dioxolanyl or the radical —N=CH—N—($C_{1-4}$-alkyl)$_2$].

Other particularly preferred carbamates (II) are those in which $R^3$ represents 2,3-dihydrobenzofuranyl, benzodioxole, benzothienyl, pyrimidinyl or pyrazolyl [each of which is optionally substituted by $C_{1-4}$-alkyl (especially methyl) or dialkylamino with 1–4 C atoms per alkyl part].

Yet further particularly preferred carbamates (II) are those in which $R^3$ represents an oxime radical of the general formula $$-O-N=C\begin{matrix}R^6\\ \\R^7\end{matrix} \qquad (IIa)$$

in which
R$^6$ and R$^7$, which may be identical or different, each represent alkyl, cycloalkyl, alkenyl, alkynyl, alkoxy, alkylmercapto, alkoxycarbonyl, carbonylamide or alkylmercaptoalkyl with up to 5 C atoms in each case, CN, aryl (especially phenyl), an optionally substituted heterocyclic radical or alkyl which is substituted by a heterocyclic radical, or R$^6$ and R$^7$ together form a dioxolanyl or dithiolanyl radical which is optionally substituted by C$_{1-4}$-alkyl.

Preferred carboxylic acid esters (B) are those of the general formula $$R^8-\overset{\overset{O}{\|}}{C}-O-\overset{\overset{R^9}{|}}{C}H-R^{10} \qquad (III)$$

in which
R$^8$ represents alkyl, aralkyl, aryl or cycloalkyl, each of which can be optionally substituted,
R$^9$ represents hydrogen, alkyl, halogenoalkyl, alkenyl, alkynyl or CN, and
R$^{10}$ represents aryl or a heterocyclic radical, or
R$^9$ and R$^{10}$ together form an optionally substituted cyclopentenone ring.

Particularly preferred carboxylic acid esters (III) are those in which
R$^8$ represents alkyl with 1–6 C atoms [which is optionally substituted by optionally halogen-substituted phenyl], cyclopropyl [which is optionally substituted by alkyl, alkenyl, halogenoalkyl or halogenoalkenyl with up to 6 C atoms in each case] or phenyl which is optionally substituted by halogen, and/or
R$^9$ represents hydrogen, alkyl with 1–6 C atoms, halogenoalkyl with 1–4 C atoms and up to 3 halogen atoms, CN or ethynyl, and/or
R$^{10}$ represents phenyl [which is optionally substituted by C$_{1-4}$-alkyl, halogen (especially fluorine or chlorine), optionally halogen- or methyl-substituted phenoxy or optionally substituted benzyl], furanyl, tetrahydrophthalimido or benzodioxole [any of which is optionally substituted by halogen (especially chlorine), alkyl or alkenyl with up to 4 C atoms or benzyl] or R$^9$ and R$^{10}$ together are cyclopentenone [which is optionally substituted by C$_{1-4}$-alkyl, furfuryl or C$_{2-5}$-alkenyl].

In addition, naturally occurring pyrethroids are particularly preferred.

Preferred phosphoric acid esters (C) are those of the general formula $$R^{11}-X-\overset{\overset{X}{\|}}{P}\begin{matrix}X-R^{12}\\ \\Y-R^{13}\end{matrix} \qquad (IV)$$

in which
each X, independently of one another, represents O or S,

Y represents O, S, —NH— or a direct bond between the central P atom and the radical R$^{13}$,
R$^{11}$ and R$^{12}$, which may be identical or different, each represent alkyl or aryl and
R$^{13}$ represents alkyl, aryl, heteroaryl, aralkyl, alkenyl, dioxanyl or an oxime radical, or represents a radical identical to that to which it is bonded.

Particularly preferred phosphoric acid esters (IV) are those in which
R$^{11}$ and R$^{12}$, which may be identical or different, each represent C$_{1-4}$-alkyl or phenyl, and
R$^{13}$ represents alkyl with 1–4 C atoms [which is optionally substituted by halogen, OH, CN, optionally halogen-substituted phenyl, carbonylamide, sulphonylalkyl, sulphoxyalkyl, carbonylalkyl, alkoxy, alkylmercapto or alkoxycarbonyl], alkenyl with up to 4 C atoms [which is optionally substituted by halogen, optionally halogen-substituted phenyl or alkoxycarbonyl] or an oxime radical of the general formula $$-O-N=C\begin{matrix}R^6\\ \\R^7\end{matrix} \qquad (IIa)$$

wherein
R$^6$ and R$^7$ have the meanings stated above (especially cyano or phenyl), or
R$^{13}$ represents dioxanyl which is substituted by a radical identical to that to which R$^{13}$ is bonded, or R$^{13}$ represents a radical identical to that to which it is bonded, or
R$^{13}$ represents phenyl [which is optionally substituted by methyl, nitro, CN, halogen or methylmercapto], or R$^{13}$ represents hetero-aromatic structures (such as pyridine, quinoline, quinoxaline, pyrimidine, diazinone or benzo-1,2,4-triazine) optionally substituted by C$_{1-4}$-alkyl or halogen.

Unless otherwise expressed, the radicals alkyl, alkenyl, alkoxy and alkenoxy as employed herein have up to 6 carbon atoms, preferably up to 4. "Lower" employed in conjunction therewith, e.g. lower alkoxy radicals, has reference to up to 4 carbon atoms, preferably up to 3. The cycloalkyl radicals have from 3 to 7, preferably 3 to 6 and especially 5 or 6 ring carbon atoms. Aryl is preferably naphthyl or, especially, phenyl.

The carbamates (group A) of the formula (II) which may be used as components of the mixture include: 2-methylphenyl, 2-ethylphenyl, 2-n-propylphenyl, 2-methoxyphenyl, 2-ethoxyphenyl, 2-iso-propoxyphenyl, 4-methylphenyl, 4-ethylphenyl, 4-n-propylphenyl, 4methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-[1,3-dioxolan-2-yl-phenyl] and 2,2-dimethyl-1,3-benzodioxol-4 -yl N-methylcarbamate and the corresponding N-methyl-N-acetyl-, N-methyl-N-trifluoromethylthio-, N-methyl-N-dichloromonofluoromethythio- and N-methyl-N-dimethylaminothio-carbamate.

These compounds, their preparation and their use are known (see, for example, U.S. Pat. Nos. 3,009,855; 2,903,478 and 3,111,539).

The carboxylic acid esters (group B) of the formula (III) which may be used as components of the mixture include: acetic acid 1-(3,4-dichlorophenyl)-2,2,2-trichloroethyl ester, 2,3,4,5-tetrahydrophthalimidomethyl chrysanthemate and (5-benzyl-3-furyl)-methyl-2,2-dimethyl-3-(2-methylpropenyl)-cyclopropanecarboxylate.

The compounds listed are known and in many cases are generally known commercial products [see. R. Wegler "Chemie der Pflanzenschutz- und Schädingsbekämpfungsmittel" ("Chemistry of Plant Protection Agents and Agents for Combating Pests"), Volume 1, pages 87-118, Heidelberg (1970)].

The phosphoric acid esters of the formula (IV) which may be used as components of the mixture include: O,O-dimethyl- and O,O-diethyl-O-(2,2-dichloro- or 2,2-dibromo-vinyl)-phosphoric acid esters.

The compounds of the formula (IV) are known and are easily producible by processes which are known from the literature (see, for example, U.S. Pat. No. 2,956,073, German Auslegeschrift (German Published Specification) No. 1,167,324 and Belgian Pat. No. 633,478).

The weight ratios of the groups of active compounds can vary within relatively wide limits. In general, the benzodioxole derivative component (i) is employed with the remaining active compound(s) (ii) in a weight ratio of about 0.1:10 to 10:0.1. However, a weight ratio of about 0.5:1.0 to 3.0:1.0 has proved particularly suitable.

The active compound combinations according to the invention not only produce a rapid knock-down action but also bring about the lasting destruction of all or some stages of development of animal pests, especially insects. The pests includes those which occur in agriculture, forestry, the protection of stored products and the protection of materials, as well as in the hygiene field. They include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentials* and *Schistocera gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes, aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

When used against hygiene pests and pests of stored products, the new compositions are distinguished by an excellent residual activity on wood and clay as well as a good stability to alkali on limed substrates.

The new compositions according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (ethylacetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The new compositions may be employed alone or in the form of mixtures with one another and/or with such solid and/or liquid dispersible carrier vehicles and/or with other known compatible active agents, especially plant protection agents, such as other arthropodicides or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the new composition is present in an amount substantially between about 0.1–95% by weight, and preferably 0.5–90% by weight, of the mixture, whereas carrier composition mixtures suitable for direct application or field application generally contemplate those in which the new composition is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the new composition which is effective for the purpose in question and which is generally between about 0.0001–95%, and preferably 0.01–95%, by weight of the mixture.

The new compositions can also be used in accordance with the well-known ultra-low-volume process with good success, i.e. by applying such compounds if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compounds or even the 100% active substance alone, e.g. about 20–100% by weight of the active compounds.

Furthermore, the present invention contemplates methods of selectively killing, combating or controlling pests, e.g. arthropods, which comprises applying to at least one of correspondingly (a) such arthropods, and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compounds of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the benzodioxoles of the present invention is illustrated, without limitation, by the following examples:

PREPARATIVE EXAMPLE 1

Alkylation of 3,4-methylenedioxyphenylacetonitrile:

1(a) 1.0 mole of 3,4-methylenedioxyphenylacetonitrile or 3,4-methylenedioxyphenyl-α-alkylacetonitrile was added dropwise to a suspension of 1.1 moles of potassium tert.-butylate in 1,500 ml of toluene at 25°–30° C., while cooling slightly. The mixture was stirred for 30 minutes at 40°–50° C. and 1.1 moles of an alkyl halide were then added dropwise at 50° C., while cooling. The mixture was stirred for 3 hours under reflux and cooled, water was added, the organic phase was washed until neutral and dried over sodium sulphate. The solvent was stripped off and the residue was distilled in vacuo.

TABLE 1

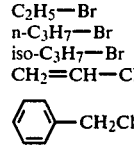

| Compound No. | Starting halide | $R^1$ | $R^2$ | Yield (% of theory) | Boiling point °C./mm Hg |
|---|---|---|---|---|---|
| (1) | $CH_3I$ | H | $CH_3$ | 66 | 138/3 |
| (2) | $C_2H_5$—Br | H | $C_2H_5$ | 76 | 147–149/4 |
| (3) | n-$C_3H_7$—Br | H | n-$C_3H_7$ | 75 | 156/3 |
| (4) | iso-$C_3H_7$—Br | H | iso-$C_3H_7$ | 78 | 133/2–3 |
| (5) | $CH_2$=CH—$CH_2$Br | H | —$CH_2$—CH=$CH_2$ | 76 | 146/3 |
| (6) | ⟨phenyl⟩—$CH_2Cl$ | H | —$CH_2$—⟨phenyl⟩ | 73 | 206/3 |
| (7) | ⟨cyclohexyl-H⟩Br | H | ⟨cyclohexyl-H⟩ | 46 | 134/1–2 |
| (8) | 2 $CH_3I$ | $CH_3$ | $CH_3$ | 85 | 134/4 |
| (9) | $C_2H_5$—Br + $CH_3I$ | $CH_3$ | $C_2H_5$ | 70 | 138/3 |

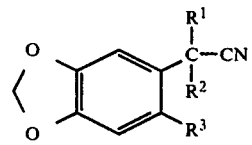

| Compound No. | Starting halide | $R^1$ | $R^2$ | $R^3$ | Yield (% of theory) | Boiling point °C./mm Hg |
|---|---|---|---|---|---|---|
| (10) | $CH_3I$ | H | $CH_3$ | n-$C_3H_7$ | 71 | 125/0.01 |
| (11) | $C_2H_5Br$ | H | $C_2H_5$ | n-$C_3H_7$ | 65 | 132/0.01 |
| (12) | n-$C_3H_7Br$ | H | n-$C_3H_7$ | n-$C_3H_7$ | 68 | 168/3 |
| (13) | iso-$C_3H_7Br$ | H | iso-$C_3H_7$ | n-$C_3H_7$ | 50 | 162/3 |
| (14) | $CH_2$=CH—$CH_2$Br | H | $CH_2$=CH—$CH_2$ | n-$C_3H_7$ | 74 | 160/3 |
| (15) | — | H | H | tert.-$C_4H_9$ | 68 | 138/0.01 |
| (16) | $CH_3I$ | H | $CH_3$ | tert.-$C_4H_9$ | 46 | 104 |
| (17) | $C_2H_5Br$ | H | $C_2H_5$ | tert.-$C_4H_9$ | 52 | 94 |
| (18) | n-$C_3H_7Br$ | H | n-$C_3H_7$ | tert.-$C_4H_9$ | 49 | 106 |
| (19) | iso-$C_3H_7Br$ | H | iso-$C_3H_7$ | tert.-$C_4H_9$ | 49 | 132/0.01 |
| (20) | — | H | H | $CH_3$ | 62 | 145/3 |
| (21) | $CH_3I$ | H | $CH_3$ | $CH_3$ | 74 | 143/3 |
| (22) | $C_2H_5Br$ | H | $C_2H_5$ | $CH_3$ | 79 | 138/1 |
| (23) | n-$C_3H_7Br$ | H | n-$C_3H_7$ | $CH_3$ | 69 | 150/2 |
| (24) | iso-$C_3H_7Br$ | H | iso-$C_3H_7$ | $CH_3$ | 71 | 143/2 |
| (25) | — | H | H | $CH_2$—CH=$CH_2$ | 61 | 110–112/0.1 |
| (26) | $CH_3I$ | H | $CH_3$ | $CH_2$—CH=$CH_2$ | 63 | 125/0.1 |
| (27) | $C_2H_5Br$ | H | $C_2H_5$ | $CH_2$—CH=$CH_2$ | 76 | 124/0.2 |
| (28) | n-$C_3H_7Br$ | H | n-$C_3H_7$ | $CH_2$—CH=$CH_2$ | 51 | 124/0.15 |
| (29) | iso-$C_3H_7Br$ | H | iso-$C_3H_7$ | $CH_2$—CH=$CH_2$ | 33 | 120/0.2 |

| Compound No. | Starting halide | $R^1$ | $R^2$ | $R^3$ | Yield (% of theory) | Boiling point °C./mm Hg melting point °C. |
|---|---|---|---|---|---|---|
| (30) | — | H | H | —CH=CH—$CH_3$ | 73 | 134/0.1  89 |
| (31) | $CH_3I$ | H | $CH_3$ | —CH=CH—$CH_3$ | 69 | 125/0.1 |
| (32) | $C_2H_5Br$ | H | $C_2H_5$ | —CH=CH—$CH_3$ | 64 | 141/0.7 |

TABLE 1-continued

| | | | | | | |
|---|---|---|---|---|---|---|
| (33) | n-C$_3$H$_7$Br | H | n-C$_3$H$_7$ | —CH=CH—CH$_3$ | 66 | 149/0.7 |
| (34) | iso-C$_3$H$_7$Br | H | iso-C$_3$H$_7$ | —CH=CH—CH$_3$ | 67 | 129/0.1 |

The alkylation of the 6-alkyl-3,4-methylenedioxyphenylacetonitriles was carried out by methods analogous to that of 1(a).

1(b) By the phase-transfer catalyst method 1.0 mole of a dihalogenoalkane or alkyl halide or a dialkyl sulphate was added dropwise to a mixture of 1,000 ml of 50% strength sodium hydroxide solution, 1.0 mol of 3,4-methylenedioxyphenylacetonitrile and 10 g of a phase transfer catalyst (for example triethylbenzylammonium chloride) at 40°–50° C. The mixture was stirred for 2 hours at 90° C., cooled, poured into 1,500 ml of ice-water and extracted with methylene chloride. The methylene chloride solution was washed until neutral and dried, the solvent was stripped off and the residue was distilled.

TABLE 2

| Compound No. | Alkylating agent | Yield (% of theory) | Boiling point °C./mm Hg |
|---|---|---|---|
| 35 | Br—CH$_2$—CH$_2$—Br | 19 | 130/3 |
| 36 | Cl—CH$_2$—CH$_2$—CH$_2$—CH$_2$—Cl | 58 | 155/3 |
| 37 | (C$_2$H$_5$O)$_2$SO$_2$ | 34 | 148/4 |

Halogenation of the 3,4-methylenedioxyphenyl-α-alkyl-acetonitriles

2(a) Chlorination with sulphuryl chloride 0.11 mole of sulphuryl chloride was added dropwise to 0.1 mole of a 3,4-methylenedioxyphenyl-α-alkylacetonitrile, dissolved in 100 ml of methylene chloride, at room temperature. The mixture was then stirred for 2 hours under reflux, cooled, washed with water, sodium bicarbonate solution and then with water until neutral and dried over calcium chloride. The solvent was stripped off and the residue was distilled or slightly distilled or recrystallized.

TABLE 3

$R^1$, C—CN, $R^2$, Cl on benzodioxole ring

| Compound No. | R$^1$ | R$^2$ | Yield (% of theory) | Boiling point °C./mm Hg melting point °C. |
|---|---|---|---|---|
| 38 | H | CH$_3$ | 61 | 152/4 |
| 39 | H | C$_2$H$_5$ | 91 | 158/4 |
| 40 | H | n-C$_3$H$_7$ | 74 | 165/4 |
| 41 | H | iso-C$_3$H$_7$ | 81 | 163/4 |
| 42 | CH$_3$ | CH$_3$ | 83 | 162–165/4 |
| 43 | —CH$_2$—CH$_2$—CH$_2$—CH$_2$— | | 70 | 83 |
| 44 | H | CH$_2$—C$_6$H$_5$ | 87 | 84 |
| 45 | CH$_3$ | C$_2$H$_5$ | 72 | 150/4 |

(b) Bromination

A solution of 0.105 mole of bromine in 10 ml of glacial acetic acid was added dropwise to a solution of 0.1 mole of a 3,4-methylenedioxyphenyl-α-alkylacetonitrile in 150 ml of glacial acetic acid at room temperature. The mixture was stirred for 4 hours at room temperature, poured into water and extracted with methylene chloride. The methylene chloride solution was washed with sodium bicarbonate solution and then with water until neutral and dried over calcium chloride. The solvent was stripped off and the solid residue was distilled or recrystallized.

TABLE 4

$R^1$, C—CN, $R^2$, Br on benzodioxole ring

| Compound No. | R$^1$ | R$^2$ | Yield (% of theory) | Boiling point °C./mm Hg |
|---|---|---|---|---|
| 46 | H | CH$_3$ | 55 | 158/4 |
| 47 | H | C$_2$H$_5$ | 54 | 158–160/3 |
| 48 | H | n-C$_3$H$_7$ | 45 | 160–164/4 |
| 49 | H | iso-C$_3$H$_7$ | 71 | 160/4 |
| 50 | CH$_3$ | CH$_3$ | 58 | 156/4 |

(3) Nitration

A mixture of 12 ml of concentrated sulphuric acid and 10 ml of nitric acid was added dropwise to 0.1 mole of a 3,4-methylenedioxyphenyl-α-alkyl-acetonitrile in 100 ml of glacial acetic acid at 20°–30° C., while cooling slightly, and the mixture was stirred for 3 hours at room temperature and poured into ice-water. The working-up could be carried out by (a) filtering off the precipitate which had separated out, washing it until neutral and drying it, or (b) taking it up in methylene chloride, washing the methylene chloride solution with sodium bicarbonate solution and then with water until neutral and drying it, then stripping off the solvent and slightly distilling the remaining oil or triturating it with petroleum ether and filtering off and drying the solid yellow precipitate.

TABLE 5

$R^1$, C—CN, $R^2$, NO$_2$ on benzodioxole ring

| Compound No. | R$^1$ | R$^2$ | Physical data (melting point °C.; refractive index; boiling point °C./mm Hg) | Yield (% of theory) |
|---|---|---|---|---|
| 51 | H | CH$_3$ | n$_D^{20}$:1.5890 | 68 |
| 52 | H | H | 114 | 85 |
| 53 | H | C$_2$H$_5$ | n$_D^{20}$:1.5757 | 60 |
| 54 | H | n-C$_3$H$_7$ | 196/4 | 81 |
| 55 | H | iso-C$_3$H$_7$ | 72 | 77 |
| 56 | CH$_3$ | CH$_3$ | 126 | 74 |
| 57 | —CH$_2$—CH$_2$—CH$_2$—CH$_2$— | | 81 | 96 |
| 58 | H | —CH$_2$—C$_6$H$_5$ | 161 | 87 |
| 59 | H | —CH$_2$—CH=CH$_2$ | 104 | 54 |

The examples which follow show the synergistic properties of the benzodioxole derivatives which can be used according to the invention, in connection with the following known active compounds:

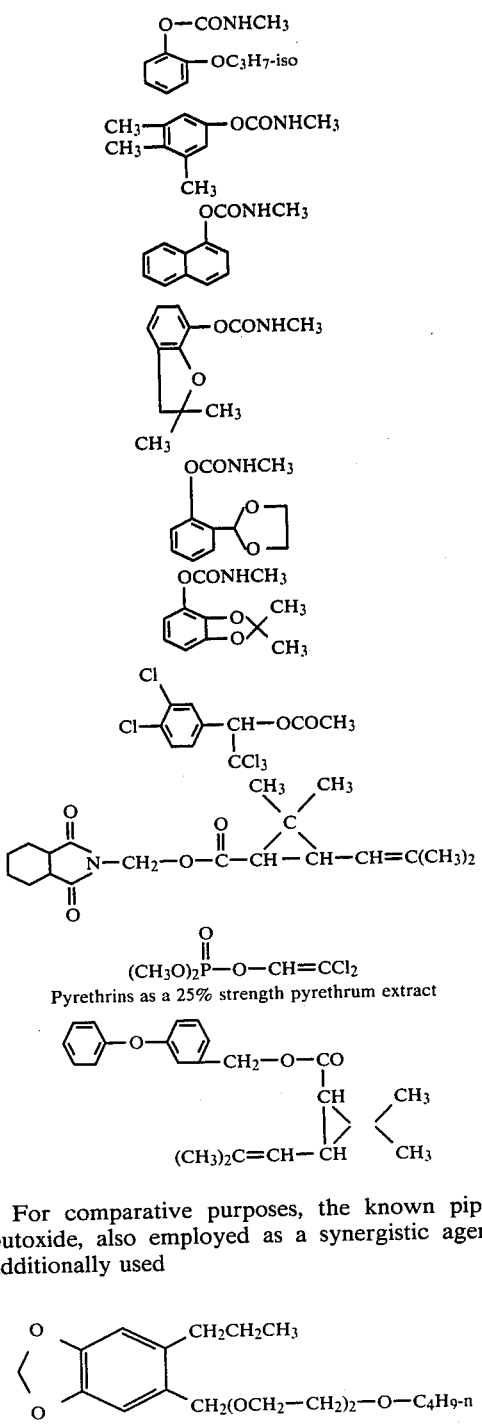

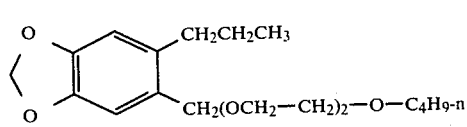

Pyrethrins as a 25% strength pyrethrum extract

For comparative purposes, the known piperonylbutoxide, also employed as a synergistic agent, was additionally used (L)

In the tables of the examples which follow, the known active compounds and the known synergistic agent have been characterized by the capital letters given above, while each synergistic agent of the formula (I) is identified by the number from the preparative example hereinabove.

EXAMPLE 2

LT₁₀₀ test

Test insects: Female *Musca domestica*, Weymann's strain, which are resistant to phosphoric acid esters Solvent: acetone Solutions of the active compounds, synergistic agents and mixtures of active compounds and synergistic agents were prepared and 2.5 ml thereof were pipetted onto filterpaper discs of 9.5 cm diameter in Petri dishes. The filterpaper absorbed the solutions. The Petri dishes were left standing open until the solvent had completely evaporated. 25 test insects were then placed in each Petri dish, and the dishes were covered with a glass lid.

The condition of the test insects was checked continuously for up to 6 hours. The time required for a 100% knock-down action was determined. If the $LT_{100}$ was not reached after 6 hours, the % of test insects which had been knocked down was ascertained.

The concentrations of the active compounds, synergistic agents and mixtures, and their actions, can be seen from the table which follows:

TABLE 6

$LT_{100}$ test with female *Musca domestica* (Weymanns strain) which are resistant to phosphoric acid esters

| Active compounds/<br>synergistic agents | Concentrations in % | $LT_{100}$ in minutes |
|---|---|---|
| A | 1.0 | 360 = 0% |
| B | 1.0 | 360 = 0% |
| C | 1.0 | 360 = 0% |
| D | 1.0 | 360 = 20% |
| E | 1.0 | 360 = 10% |
| F | 1.0 | 360 = 30% |
| G | 1.0 | 360 = 20% |
| H | 0.04 | 260 = 95% |
| J | 0.04 | 360 = 90% |
| K | 0.04 | 120' |
| L | 1.0 | 360 = 0% |
| 1 | 0.2 | 210' |
| 2 | 1.0 | 360 = 95% |
| 3 | 1.0 | 360 = 80% |
| 4 | 1.0 | 360 = 90% |
| 35 | 0.2 | 360 |
| 37 | 1.0 | 360 |
| 38 | 1.0 | 360 = 80% |
| 39 | 1.0 | 360 = 0% |
| 40 | 1.0 | 360 = 0% |
| 45 | 1.0 | 360 = 25% |
| 46 | 1.0 | 360 = 20% |
| A + L | 0.2 + 0.2 | 360 = 85% |
| A + 4 | 0.008 + 0.008 | 360 |
| A + 40 | 0.04 + 0.04 | 240 |
| A + 2 | 0.04 + 0.04 | 150 |
| A + 3 | 0.04 + 0.04 | 150 |
| A + 38 | 0.008 + 0.008 | 360 = 90% |
| A + 1 | 0.008 + 0.008 | 240 |
| A + 45 | 0.008 + 0.008 | 360 |
| B + L | 1.0 + 1.0 | 360 = 90% |
| B + 4 | 0.04 + 0.04 | 360 = 90% |
| B + 2 | 0.2 + 0.2 | 240 |
| B + 3 | 0.2 + 0.2 | 360 |
| B + 38 | 0.04 + 0.04 | 360 = 85% |
| B + 1 | 0.2 + 0.2 | 240 |
| B + 37 | 0.04 + 0.04 | 360 |
| B + 39 | 0.04 + 0.04 | 360 = 90% |
| B + 46 | 0.2 + 0.2 | 240 |
| B + 45 | 0.04 + 0.04 | 360 |
| C + L | 1.0 + 1.0 | 360 = 40% |
| C + 38 | 0.2 + 0.2 | 360 = 90% |
| C + 1 | 0.2 + 0.2 | 180 |
| C + 46 | 1.0 + 1.0 | 360 |
| C + 45 | 0.2 + 0.2 | 360 = 95% |
| D + L | 0.2 + 0.2 | 360 = 75% |
| D + 4 | 0.008 + 0.008 | 360 |
| D + 2 | 0.008 + 0.008 | 240 |
| D + 35 | 0.008 + 0.008 | 180 |
| D + 3 | 0.04 + 0.04 | 180 |
| D + 38 | 0.008 + 0.008 | 240 |
| D + 1 | 0.008 + 0.008 | 150 |
| D + 37 | 0.008 + 0.008 | 210 |
| D + 39 | 0.008 + 0.008 | 240 |
| D + 46 | 0.008 + 0.008 | 360 |

TABLE 6-continued

LT$_{100}$ test with female *Musca domestica* (Weymanns strain) which are resistant to phosphoric acid esters

| Active compounds/ synergistic agents | Concentrations in % | LT$_{100}$ in minutes |
|---|---|---|
| D + 45 | 0.008 + 0.008 | 210 |
| E + L | 0.2 + 0.2 | 360 |
| E + 4 | 0.2 + 0.2 | 240 |
| E + 2 | 0.2 + 0.2 | 360 |
| E + 35 | 0.04 + 0.04 | 360 |
| E + 3 | 0.2 + 0.2 | 210 |
| E + 38 | 0.04 + 0.04 | 360 = 95% |
| E + 1 | 0.2 + 0.2 | 150 |
| E + 37 | 0.04 + 0.04 | 360 = 90% |
| E + 46 | 0.2 + 0.2 | 240 |
| E + 45 | 0.2 + 0.2 | 360 = 70% |
| F + L | 0.008 + 0.008 | 360 |
| F + 4 | 0.008 + 0.008 | 360 |
| F + 2 | 0.008 + 0.008 | 210 |
| F + 35 | 0.04 + 0.04 | 180 |
| F + 3 | 0.008 + 0.008 | 180 |
| F + 38 | 0.008 + 0.008 | 360 |
| F + 1 | 0.008 + 0.008 | 180 |
| F + 37 | 0.008 + 0.008 | 360 |
| F + 46 | 0.008 + 0.008 | 240 |
| F + 45 | 1.0 + 1.0 | 360 = 70% |
| G + L | 0.04 + 0.04 | 360 = 85% |
| G + 4 | 0.04 + 0.04 | 360 |
| G + 2 | 0.04 + 0.04 | 360 = 95% |
| G + 35 | 0.2 + 0.2 | 360 |
| G + 3 | 0.2 + 0.2 | 360 = 90% |
| G + 38 | 0.04 + 0.04 | 360 |
| G + 1 | 0.2 + 0.2 | 360 |
| G + 46 | 0.04 + 0.04 | 360 |
| G + 45 | 0.04 + 0.04 | 90 |
| H + 4 | 0.04 + 0.04 | 105 |
| H + 35 | 0.04 + 0.04 | 105 |
| H + 38 | 0.04 + 0.04 | 180 |
| H + 37 | 0.04 + 0.04 | 150 |
| H + 39 | 0.04 + 0.04 | 105 |
| J + 4 | 0.04 + 0.04 | 180 |
| J + 35 | 0.04 + 0.04 | 240 |
| J + 38 | 0.04 + 0.04 | 150 |
| J + 39 | 0.04 + 0.04 | 180 |
| J + 37 | 0.04 + 0.04 | 90 |
| K + L | 0.04 + 0.04 | 45 |
| K + 4 | 0.04 + 0.04 | 60 |
| K + 38 | 0.04 + 0.04 | 60 |
| K + 37 | 0.04 + 0.04 | 60 |
| K + 39 | 0.04 + 0.04 | 60 |

EXAMPLE 3

LT$_{100}$ test

Test insects: *Blattella germanica* female (normally sensitive), *Blattella germanica* female (resistant), *Tribolium confusum*, *Dermestes peruvianus*, *Attagenus piceus* larvae, *Ornithodoros moubata* larvae Solvent: Acetone Solutions of the active compounds, synergistic agents and mixtures of active compounds and synergistic agents were prepared and 2.5 ml thereof were pipetted onto filterpaper of 9.5 cm diameter in Petri dishes. The filterpaper absorbed the solution. The Petri dishes were left standing open until the solvent had completely evaporated. 25 test insects were then placed in each Petri dish, and the dishes were covered with a glass lid.

The condition of the insects was checked continuously for up to 6 hours and thereafter also checked after 24, 48 and 72 hours. The time required for a 100% knock-down action was determined. If the LT$_{100}$ was not reached after 72 hours, the % of test insects which had been knocked down was ascertained.

The concentrations of the active compounds, synergistic agents and mixtures, and their actions, can be seen from the table which follows:

TABLE 7

LT$_{100}$ Test with various pests

| Active compound | Synergistic agent | Pest | Concentrations in % Active compound | Synergistic agent | LT$_{100}$ in minutes (') or hours (hrs) |
|---|---|---|---|---|---|
| A | | *Blattella germ.* female (normally sensitive) | 0.008 | | 24 hrs = 80% |
| A | | *Blattella germ.* female | 0.008 | | 24 hrs = 60% |
| | 4 | *Blattella germ.* female (normally sensitive) | | 1.0 | 24 hrs = 0% |
| A | + 4 | *Blattella germ.* female (normally sensitive) | 0.008 | + 0.008 | 60' |
| A | + 4 | *Blattella germ.* female (resistant) | 0.008 | + 0.04 | 6 hrs |
| A | | *Tribolium conf.* | 0.2 | | 72 hrs = 50% |
| | 4 | *Tribolium conf.* | | 0.2 | 72 hrs = 0% |
| A | 4 | *Tribolium conf.* | 0.04 | + 0.04 | 72 hrs = 90% |
| A | | *Dermestes peruvian.* | 0.04 | | 72 hrs = 0% |
| | 4 | *Dermestes peruvian.* | | 0.2 | 72 hrs = 0% |
| | L | *Dermestes peruvian.* | | 0.2 | 72 hrs = 0% |
| A | + L | *Dermestes peruvian.* | 0.04 | + 0.04 | 72 hrs = 20% |
| A | + 4 | *Dermestes peruvian.* | 0.04 | + 0.04 | 24 hrs |
| A | | *Attagenus piceus* larvae | 0.2 | | 72 hrs = 0% |
| | 4 | *Attagenus piceus* larvae | | 0.2 | 72 hrs = 0% |
| | L | *Attagenus piceus* larvae | | 0.2 | 72 hrs = 0% |
| A | + L | *Attagenus piceus* larvae | 0.2 | + 0.2 | 72 hrs = 0% |
| A | + 4 | *Attagenus piceus* larvae | 0.2 | + 0.2 | 24 hrs |
| A | | *Ornithodoros moubata* larvae | 0.008 | | 72 hrs = 80% |
| | L | *Ornithodoros moubata* larvae | | 1.0 | 72 hrs = 0% |
| A | + L | *Ornithodoros moubata* larvae | 0.008 | + 0.008 | 72 hrs |
| | 2 | *Ornithodoros moubata* larvae | | 1.0 | 72 hrs = 0% |
| A | + 2 | *Ornithodoros moubata* larvae | 0.008 | + 0.008 | 24 hrs |
| | 3 | *Ornithodoros moubata* larvae | | 1.0 | 72 hrs = 80% |
| A | + 3 | *Ornithodoros moubata* larvae | 0.008 | + 0.008 | 24 hrs |
| | 38 | *Ornithodoros moubata* larvae | | 1.0 | 72 hrs = 0% |

TABLE 7-continued

LT₁₀₀ Test with various pests

| Active compound | | Synergistic agent | Pest | Concentrations in % | | LT₁₀₀ in |
| --- | --- | --- | --- | --- | --- | --- |
| | | | | Active compound | Synergistic agent | minutes (') or hours (hrs) |
| A | + | 38 | Ornithodoros moubata larvae | 0.008 | + 0.008 | 120' |
| | | 1 | Ornithodoros moubata larvae | | 1.0 | 72 hrs = 0% |
| A | + | 1 | Ornithodoros moubata larvae | 0.008 | + 0.008 | 150 |
| | | 45 | Ornithodoros moubata larvae | | 1.0 | 72 hrs = 0% |
| A | + | 45 | Ornithodoros moubata larvae | 0.008 | + 0.008 | 105' |

EXAMPLE 4

Aerosol Test

Test insects: Male and female *Musca domestica*, Weymann's strain, which are resistant to phosphoric acid esters Solvent: Acetone To produce a suitable preparation of active compound, the active compounds were dissolved in the solvent.

A wire cage containing about 25 test insects was suspended in the middle of a gas-tight glass chamber of size 1 m³. When the chamber had again been closed, 2 ml of the active compound preparation were atomised therein. The condition of the test insects was constantly checked from outside, through the glass walls, and the time required for a 100% knock-down action on the insects was determined. After 60 minutes, the test insects were taken from the test chambers, transferred to an atmosphere free from the active compound, and again checked after 24 hours.

The active compounds, amounts of active compounds and times at which a 100% knock-down action was achieved, and the percentage of the insects which were dead after 24 hours, can be seen from the table which follows:

TABLE 8

Aerosol test with female *Musca Domestica* (Weymann's strain) which are resistant to phosphoric acid esters

| Active compound | Synergistic agent | Concentration in mg/m³ of air | | | LT₁₀₀ in minutes | % of dead insects after 24 hours |
| --- | --- | --- | --- | --- | --- | --- |
| | | Active compound | | Synergistic agent | | |
| I | | 5 | | | 60 = 32% | 40 |
| K | | 5 | | | 42'13" | 95 |
| | L | | | 10 | 60 = 0% | 0 |
| | 37 | | | 10 | 60 = 0% | 0 |
| I | L | 5 | | 5 | 60 = 0% | 5 |
| I | 37 | 5 | | 5 | 60 = 68% | 90 |
| K | 37 | 5 | | 5 | 33'10" | 100 |
| A | | 10 | | | 60 = 0% | 0 |
| | L | | | 10 | 60 = 0% | 0 |
| | 4 | | | 10 | 60 = 0% | 0 |
| | 3 | | | 10 | 60 = 0% | 0 |
| | 1 | | | 10 | 60 = 0% | 0 |
| | 37 | | | 10 | 60 = 0% | 0 |
| A | L | 10 | + | 10 | 60 = 0% | 0 |
| A | 3 | 10 | + | 10 | 60 = 33% | 90 |
| A | 1 | 5 | + | 5 | 60 = 93% | 70 |
| A | 1 | 10 | + | 2.5 | 45'23" | 100 |
| A | 37 | 10 | + | 10 | 60 = 70% | 100 |
| A | 37 | 10 | + | 2.5 | 60 = 63% | 90 |
| A | 4 | 10 | + | 10 | 60 = 73% | 10 |

It will be appreciated that the instant specification and examples are set forth by way of illustration and not limitation, and that various modifications and changes may be made without departing from the spirit and scope of the present invention.

What is claimed is:

1. An arthropidicidal composition containing as active compounds (i) a benzodioxole of the formula

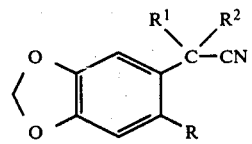

in which

R is hydrogen, alkyl or alkenyl with up to 6 carbon atoms, halogen or nitro,

R¹ is alkyl with 1 to 3 carbon atoms or hydrogen, and

R² is aryl-C₁₋₃-alkyl, alkyl or alkenyl with up to 6 carbon atoms, or cycloalkyl with 3 to 8 carbon atoms, or may represent hydrogen provided that R represents alkyl, alkenyl or nitro, or R¹ and R² together are an alkylene radical with 2 to 8 carbon atoms, and (ii) at least one arthropodicidal carboxylic acid ester or phosphoric acid ester, the weight ratio of component (i) to component (ii) ranging from about 0.1:10 to 10:0.1.

2. A composition according to claim 1, in which

R is hydrogen, chlorine, bromine, nitro or alkyl or alkenyl with up to 6 carbon atoms, R¹ is hydrogen or alkyl with 1 to 3 carbon atoms, R² is alkyl or alkenyl with up to 6 carbon atoms, cycloalkyl with 3 to 8 carbon atoms or benzyl or may represent hydrogen provided that R represents nitro, alkyl or alkenyl, or R¹ and R² together are an alkylene radical with 2 to 8 carbon atoms.

3. A composition according to claim 1, wherein the carboxylic acid ester when present is of the formula

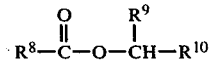

in which

R⁸ is optionally substituted alkyl, aralkyl, aryl or cycloalkyl,

R⁹ is hydrogen, alkyl, halogenoalkyl, alkenyl, alkynyl or CN, and

R¹⁰ is aryl or a heterocyclic radical, or

R⁹ and R¹⁰ together form an optionally substituted cyclopentenone ring, and the phosphoric acid ester when present is of the formula $$R^{11}-X-\overset{\overset{X}{\|}}{P}\overset{X-R^{12}}{\underset{Y-R^{13}}{}}$$

in which
each X is O or S,
Y is O, S, —NH— or a direct bond between the central P atom and the radical $R^{13}$,
$R^{11}$ and $R^{12}$ each independently is alkyl or aryl, and
$R^{13}$ is alkyl, aryl, heteroaryl, aralkyl, alkenyl, dioxanyl or an oxime radical, or is a radical identical to that to which it is bonded.

4. A composition according to claim 3, wherein
$R^8$ is alkyl with 1–6 C atoms optionally substituted by optionally halogen-substituted phenyl, cyclopropyl which is optionally substituted by alkyl, alkenyl, halogenoalkyl or halogenoalkenyl with up to 6 C atoms in each hydrocarbyl moiety; phenyl or halophenyl;
$R^9$ is hydrogen, $C_{1-6}$-alkyl, halogenoalkyl with 1–4 C atoms and up to 3 halogen atoms, CN or ethynyl, and
$R^{10}$ is phenyl, phenyl substituted by $C_{1-4}$-alkyl, halogen, phenoxy, halophenoxy, methyl-phenoxy, or optionally substituted benzyl; furanyl, tetrahydrophthalimido or benzodioxole optionally substituted by halogen, alkyl or alkenyl with up to 4 C atoms or benzyl; or cyclopentenone optionally substituted by $C_{1-4}$-alkyl, furfuryl or $C_{2-5}$-alkenyl,
$R^{11}$ and $R^{12}$ each independently is $C_{1-4}$-alkyl or phenyl, and
$R^{13}$ is $C_{1-4}$-alkyl optionally substituted by halogen, OH, CN, phenyl, halophenyl, carbonylamide, sulphonylalkyl, sulphoxyalkyl, carbonylalkyl, alkoxy, alkylmercapto or alkoxycarbonyl, alkenyl with up to 4 C atoms optionally substituted by halogen, phenyl, halophenyl, alkoxycarbonyl, an oxime radical of the formula $$-O-N=C\overset{R^6}{\underset{R^7}{}}$$

dioxanyl which is substituted by a radical identical to that to which $R^{13}$ is bonded, a radical identical to that to which it is bonded, phenyl optionally substituted by methyl, nitro, CN, halogen or methylmercapto, or a hetero-aromatic structure optionally substituted by $C_{1-4}$-alkyl or halogen, and
$R^6$ and $R^7$ each independently is alkyl, cycloalkyl, alkenyl, alkynyl, alkoxy, alkylmercapto, alkoxycarbonyl, carbonylamide or alkylmercaptoalkyl with up to 5 C atoms in each hydrocarbyl moiety, CN, aryl, an optionally substituted heterocyclic radical or alkyl which is substituted by a heterocyclic radical, or
$R^6$ and $R^7$ together form a dioxolanyl or dithiolanyl radical which is optionally substituted by $C_{1-4}$-alkyl.

5. A composition according to claim 3, in which
$R^8$ is alkyl or an alkyl-substituted or alkenyl-substituted cyclopropyl ring,
$R^9$ is hydrogen or halogenoalkyl,
$R^{10}$ is aryl, haloaryl or a heterocyclic radical,
X and Y each is oxygen,
$R^{11}$ and $R^{12}$ each is $C_{1-4}$-alkyl, and
$R^{13}$ is $-CH=C(Halogen)_2$.

6. A composition according to claim 1, in which the weight ratio of component (i) to component (ii) is from about 0.5:1 to 3:1.

7. A composition according to claim 1, wherein $R^2$ is aralkyl, alkyl, alkenyl or cycloalkyl.

8. A composition according to claim 1, wherein R is alkyl, alkenyl or nitro, and $R^2$ is aralkyl, alkyl, alkenyl, cycloalkyl or hydrogen.

9. A composition according to claim 1, wherein component (i) is α-methyl-3,4-methylenedioxyphenylacetonitrile.

10. A composition according to claim 1, wherein component (i) is α-isopropyl-3,4-methylenedioxyphenylacetonitrile.

11. A composition according to claim 1, wherein component (i) is α-methyl-6-chloro-3,4-methylenedioxyphenylacetonitrile.

12. A composition according to claim 1, wherein component (i) is α-ethyl-6-chloro-3,4-methylenedioxyphenylacetonitrile.

13. A composition according to claim 1, wherein component (i) is α,α-dimethyl-6-chloro-3,4-methylenedioxyphenylacetonitrile.

14. A composition according to claim 1, wherein component (i) is α-methyl-6-bromo-3,4-methylenedioxyphenylacetonitrile.

15. A composition according to claim 1, wherein component (i) is α-ethyl-6-bromo-3,4-methylenedioxyphenylacetonitrile.

16. A composition according to claim 1, wherein component (ii) comprises a carboxylic acid ester.

17. A composition according to claim 1, wherein component (ii) comprises a phosphoric acid ester.

18. A method of combating arthropods which comprises applying to the arthropods, or to a habitat thereof, an arthropicidally effective amount of a composition according to claim 1.

* * * * *